US00PP18678P2

(12) United States Plant Patent
Oudolf

(10) Patent No.: US PP18,678 P2
(45) Date of Patent: Apr. 1, 2008

(54) ***ECHINACEA* PLANT NAMED 'GREEN JEWEL'**

(50) Latin Name: *Echinacea purpurea*
Varietal Denomination: Green Jewel

(75) Inventor: Petrus Hendricus Oudolf, Hummelo (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/637,856

(22) Filed: Dec. 12, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Echinacea* plant named 'Green Jewel', characterized by its compact and upright plant habit; moderately vigorous growth habit; freely flowering habit; large single inflorescences with light green-colored ray florets; and strong peduncles that hold the inflorescences above the foliar plane.

2 Drawing Sheets

Botanical designation: *Echinacea purpurea.*
Cultivar denomination: 'Green Jewel'.

BACKGROUND OF THE INVENTION

The present invention relates to a new and distinct cultivar of *Echinacea* plant, botanically known as *Echinacea purpurea,* and hereinafter referred to by the name 'Green Jewel'.

The new *Echinacea* originated from an open-pollination of an unnamed selection of *Echinacea purpurea,* not patented, as the female, or seed, parent with an unknown selection of *Echinacea purpurea,* as the male, or pollen, parent. The new *Echinacea* was discovered and selected by the Inventor as a single flowering plant from within the progeny of the stated open-pollination grown in a controlled environment in Hummelo, The Netherlands in 2004.

Asexual reproduction of the new *Echinacea* by divisions in a controlled environment in Hummelo, The Netherlands since 2005, has shown that the unique features of this new *Echinacea* are stable and reproduced true to type in successive generations.

SUMMARY OF THE INVENTION

The cultivar Green Jewel has not been observed under all possible environmental conditions. The phenotype may vary somewhat with variations in environment such as temperature and light intensity, without, however, any variance in genotype.

The following traits have been repeatedly observed and are determined to be the unique characteristics of 'Green Jewel'. These characteristics in combination distinguish 'Green Jewel' as a new and distinct cultivar of *Echinacea:*

1. Compact and upright plant habit.
2. Moderately vigorous growth habit.
3. Freely flowering habit.
4. Large single inflorescences with light green-colored ray florets.

5. Strong peduncles that hold the inflorescences above the foliar plane.

Compared to plants of the female parent selection, plants of the new *Echinacea* are more compact and are more freely flowering.

Plants of the new *Echinacea* can be compared to plants of the *Echinacea* cultivar Jade, disclosed in U.S. Plant Pat. No. 13,769. In side-by-side comparisons conducted in Lisserbroek, The Netherlands, plants of the new *Echinacea* differed from plants of the cultivar Jade primarily in ray floret coloration as plants of the cultivar Jade had white-colored ray florets.

BRIEF DESCRIPTION OF THE PHOTOGRAPHS

The accompanying photographs illustrate the overall appearance of the new *Echinacea.* These photographs show the colors as true as it is reasonably possible to obtain in colored reproductions of this type. Colors in the photographs may differ slightly from the color values cited in the detailed botanical description which accurately describe the colors of the new *Echinacea.*

The photograph on the first sheet comprises a side perspective view of a typical flowering plant of 'Green Jewel' grown in an outdoor nursery.

The photograph at the top of the second sheet is a close-up view of a typical inflorescence of 'Green Jewel'.

The photograph at the bottom of the second sheet is a close-up view of a typical leaf of 'Green Jewel'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in Lisserbroek, The Netherlands during the summer in an outdoor nursery and under conditions and practices which approximate those generally used in commercial *Echinacea* production. During the production of the plants, day temperatures ranged from 18° C. to 35° C. and night temperatures ranged from 10° C. to 20° C. Measurements and numerical values represent averages for typical flowering plants. Plants were about two years old when the photographs and description were taken.

Botanical classification: *Echinacea purpurea* cultivar Green Jewel.

Parentage:

*Female parent.*—Unnamed selection of *Echinacea purpurea,* not patented.

*Male parent.*—Unknown selection of *Echinacea purpurea,* not patented.

Propagation:

*Type.*—By divisions.

*Time to produce a rooted young plant.*—About two months at 18° C. to 20° C.

*Root description.*—Fine, fibrous; light brown to white in color.

*Rooting habit.*—Freely branching; moderately dense.

Plant description:

*Plant form/growth habit.*—Compact, upright and uniform plant habit; inverted triangle; freely basal branching with inflorescences held above the foliage on strong peduncles. Moderately vigorous growth habit.

*Plant height.*—About 74.5 cm.

*Plant diameter or spread.*—About 49.3 cm.

*Lateral branches.*—Length: About 70.3 cm. Diameter: About 6 mm. Internode length: About 5.1 cm. Aspect: Mostly upright. Strength: Strong. Texture: Densely pubescent; rough. Color: 143C to 144A.

Foliage description:

*Arrangement.*—Alternate, simple; sessile.

*Length.*—About 16.7 cm.

*Width.*—About 6.5 cm.

*Shape.*—Narrowly ovate to ovate.

*Apex.*—Acute.

*Base.*—Attenuate.

*Margin.*—Irregularly serrate; undulate.

*Texture, upper and lower surfaces.*—Moderately pubescent; rough.

*Venation pattern.*—Pinnate.

*Color.*—Developing foliage, upper surface: 137B. Developing foliage, lower surface: 138B. Fully expanded foliage, upper surface: 137A to 139A; venation, 145C. Fully expanded foliage, lower surface: 137C; venation, 145C.

Inflorescence description:

*Appearance.*—Rotate single inflorescence form with ray and disc florets. Inflorescences positioned above the foliage on strong peduncles. Inflorescences face upright. Freely flowering habit; about four inflorescences develop per lateral branch. Inflorescences not persistent.

*Fragrance.*—Faint; sweet.

*Time to flower.*—Plants flower continuously from late June to mid-September in The Netherlands.

*Post-production longevity.*—Inflorescences maintain good substance for about three weeks on the plant.

*Inflorescence bud.— Height: About* 2.5 cm. Diameter: About 2.9 cm. Shape: Oblate. Color: 143A.

*Inflorescence size.*—Diameter: About 11.1 cm. Depth (height): About 4.2 cm. Disc diameter: About 5 cm. Receptacle height: About 2.5 cm. Receptacle diameter: About 2.2 cm.

*Ray florets.*—Length: About 4.5 cm. Width: About 1 cm. Shape: Oblanceolate. Apex: Praemorse to emarginate. Base: Cuneate. Texture, upper and lower surfaces: Smooth, glabrous; ribbed lengthwise. Number of ray florets per inflorescence: About 34 arranged in a single whorl. Color: When opening, upper surface: 144C. When opening, lower surface: 144B to 144C. Fully opened, upper surface: 144B; color becoming closer to 154C with development. Fully opened, lower surface: 144A to 144B; color becoming closer to 154C with development.

*Disc florets.*—Shape: Tubular; apex dentate. Length: About 1.7 cm. Diameter: About 1.5 mm. Number of disc florets per inflorescence: About 500. Texture: Smooth, glabrous. Color: Immature: 144A; towards the base, 145C. Mature: 144A; towards the base, 145C.

*Receptacle spines.*—Quantity: One per disc floret. Length: About 2 cm. Width: About 1 mm. Shape: Acicular. Apex: Sharply acute. Color: Apex: 17A. Mid-section: 144A to 144C. Base: 145D.

*Phyllaries.*—Quantity per inflorescence: About 90 in about four whorls. Length: About 1 cm. Width: About 3 mm. Shape: Lanceolate. Apex: Acute. Base: Cuneate. Margin: Entire. Texture, upper surface: Smooth, glabrous. Texture, lower surface: Densely pubescent. Color, upper surface: 137A; towards the base, 137C. Color, lower surface: 137A.

*Peduncles.*—Length: About 33.5 cm. Diameter: About 5 mm. Strength: Strong. Aspect: Mostly upright. Texture: Densely pubescent; slight rough. Color: 143A to 143B.

*Reproductive organs.*—Androecium: Quantity per disc floret: About five. Filament length: About 7 mm. Filament color: 146A. Anther shape: Linear. Anther length: About 1 mm. Anther color: 146B to 146C. Pollen amount: Moderate. Pollen color: 13A. Gynoecium: Pistil length: About 7 mm. Stigma shape: Cleft; reflexed. Stigma color: 151A. Style length: About 4 mm. Style color: 145C. Ovary color: 157D. Seeds/fruits: Seed and fruit development have not been observed.

Disease/pest resistance: Plants of the new *Echinacea* have not been shown to be resistant to pathogens and pests common to *Echinacea.*

Garden performance: Plants of the new *Echinacea* have exhibited good tolerance to rain and wind and have been observed to be suitable for USDA Zones 3 or 4 to 9.

It is claimed:

1. A new and distinct *Echinacea* plant named 'Green Jewel' as illustrated and described.

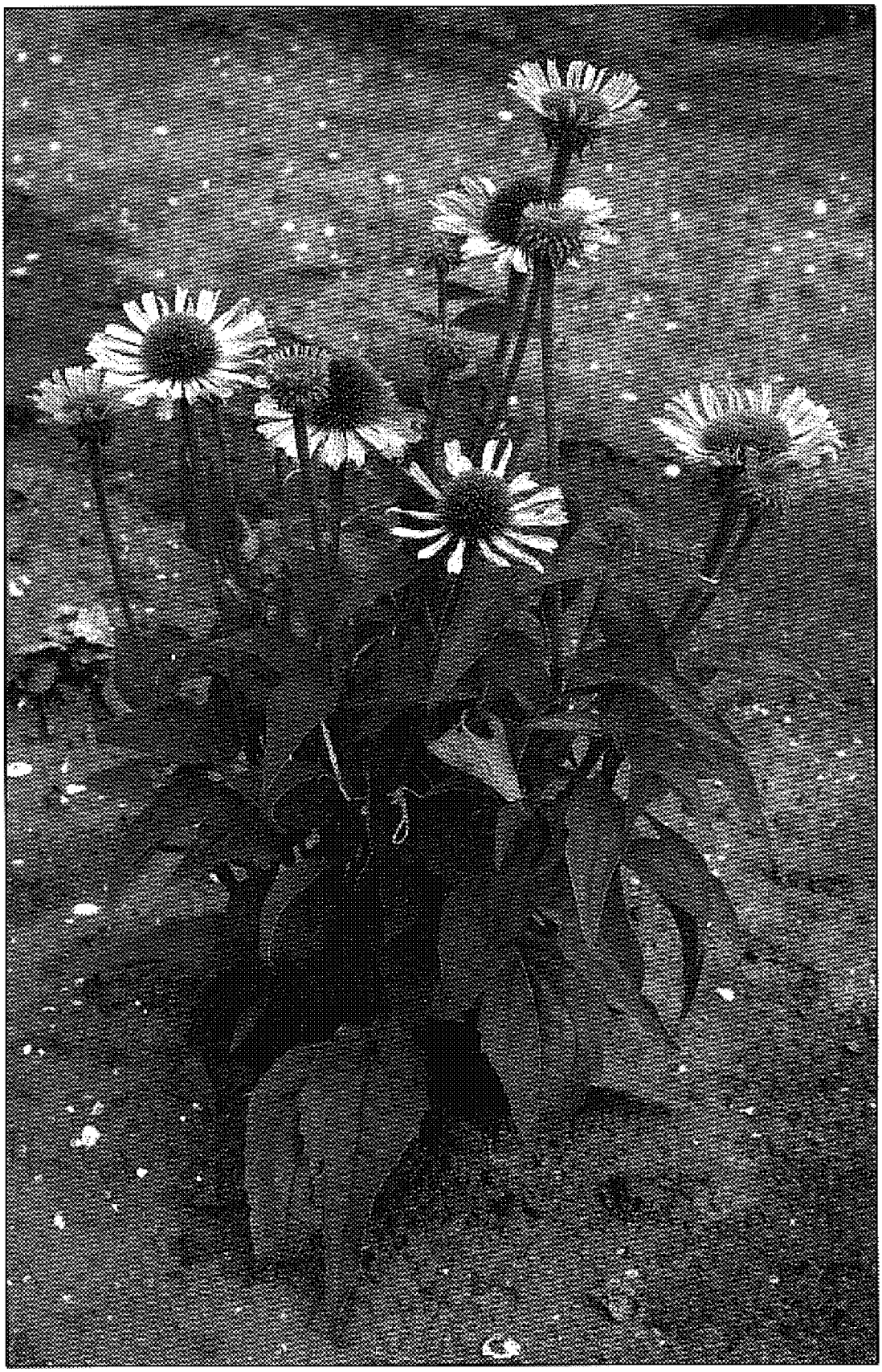

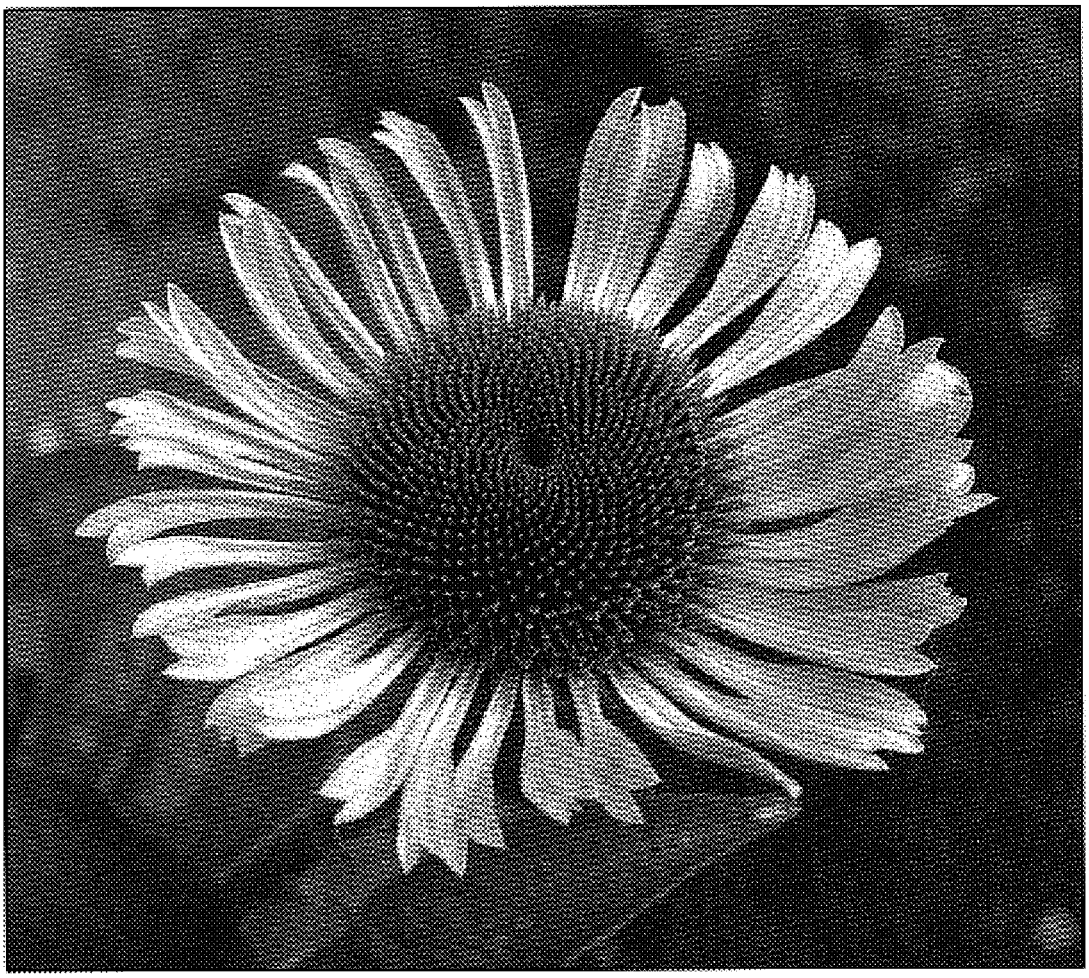
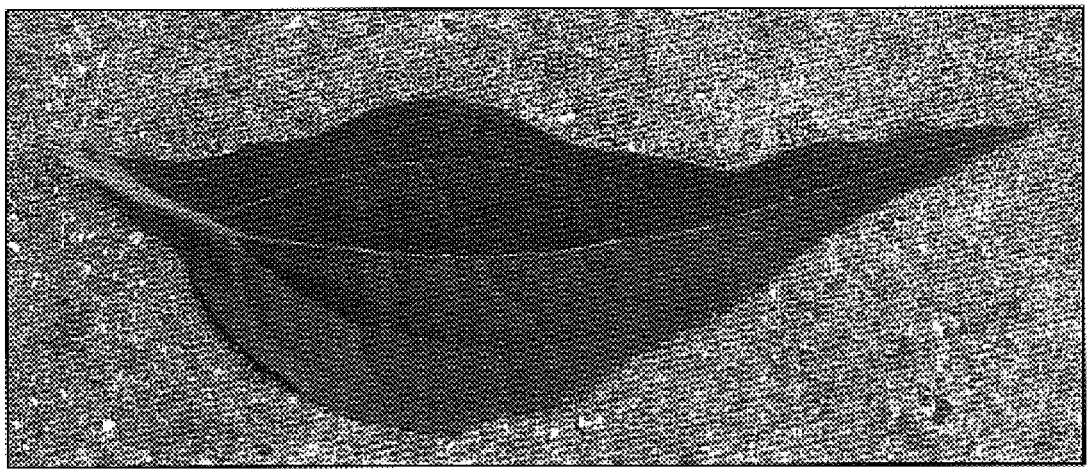

* * * * *